US010363399B2

(12) United States Patent
Chen et al.

(10) Patent No.: US 10,363,399 B2
(45) Date of Patent: Jul. 30, 2019

(54) DUAL-LAYER BALLOON DESIGN AND METHOD OF MAKING THE SAME

(71) Applicant: Boston Scientific Scimed, Inc., Maple Grove, MN (US)

(72) Inventors: John Jianhua Chen, Plymouth, MN (US); Daniel James Horn, Shoreview, MN (US); Adam Joseph Royer, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 156 days.

(21) Appl. No.: 14/870,892

(22) Filed: Sep. 30, 2015

(65) Prior Publication Data

US 2016/0089517 A1 Mar. 31, 2016

Related U.S. Application Data

(60) Provisional application No. 62/057,666, filed on Sep. 30, 2014.

(51) Int. Cl.
*A61M 25/10* (2013.01)
*B29C 49/00* (2006.01)
*A61L 29/06* (2006.01)
*B29K 67/00* (2006.01)

(52) U.S. Cl.
CPC ............. *A61M 25/10* (2013.01); *A61L 29/06* (2013.01); *A61M 25/1029* (2013.01); *B29C 49/0021* (2013.01); *A61M 2025/1075* (2013.01); *B29K 2067/003* (2013.01)

(58) Field of Classification Search
CPC .......... A61M 2025/1075; A61M 25/10; A61M 25/1029; B29K 2067/003
See application file for complete search history.

(56) References Cited

U.S. PATENT DOCUMENTS

| | | | |
|---|---|---|---|
| 5,306,246 A * | 4/1994 | Sahatjian | A61L 29/049 264/515 |
| 5,499,973 A | 3/1996 | Saab | |
| 5,613,979 A | 3/1997 | Trotta et al. | |
| 5,755,690 A | 5/1998 | Saab | |
| 6,132,824 A | 10/2000 | Hamlin | |
| 6,136,258 A | 10/2000 | Wang et al. | |
| 6,706,538 B1 | 3/2004 | Karg et al. | |
| 6,780,193 B2 | 8/2004 | Leslie et al. | |
| 6,951,557 B2 | 10/2005 | Ellis et al. | |
| 6,989,071 B2 | 1/2006 | Kocur et al. | |
| 6,997,946 B2 | 2/2006 | Girton et al. | |
| 7,029,732 B2 | 4/2006 | Wang et al. | |
| 7,094,249 B1 | 8/2006 | Broome et al. | |
| 7,128,862 B2 | 10/2006 | Wang | |

(Continued)

*Primary Examiner* — Deanna K Hall
(74) *Attorney, Agent, or Firm* — Seager, Tufte & Wickhem LLP.

(57) ABSTRACT

An expandable medical balloon, the expandable medical balloon comprising a first balloon wall, the first balloon wall comprising a first balloon layer of polyethylene terephthalate having a first intrinsic viscosity, the first layer is outer to a second layer of polyethylene terephthalate, the second balloon layer of polyethylene terephthalate having a second intrinsic viscosity, the second layer is an inner layer, wherein the intrinsic viscosity of the first balloon layer is higher than the intrinsic viscosity of the second balloon layer by about 0.05 dl/g or more.

15 Claims, 1 Drawing Sheet

(56) References Cited

U.S. PATENT DOCUMENTS

| | | |
|---|---|---|
| 7,166,099 B2 | 1/2007 | Devens, Jr. |
| 7,217,278 B2 | 5/2007 | Tomaschko et al. |
| 7,244,271 B2 | 7/2007 | Lentz et al. |
| 7,261,734 B2 | 8/2007 | Gellman et al. |
| 7,294,417 B2 | 11/2007 | Ren et al. |
| 7,387,826 B2 * | 6/2008 | Burgmeier ............... A61L 29/14 428/35.7 |
| 7,476,034 B2 | 1/2009 | Shedlov et al. |
| 7,481,804 B2 | 1/2009 | Devens, Jr. |
| 7,488,339 B2 | 2/2009 | St. Pierre et al. |
| 7,585,289 B2 | 9/2009 | Wang et al. |
| 7,591,825 B2 | 9/2009 | Leslie et al. |
| 7,597,775 B2 | 10/2009 | Sogard et al. |
| 7,608,101 B2 | 10/2009 | Gellman et al. |
| 7,771,450 B2 | 8/2010 | Tomascko et al. |
| 7,789,908 B2 | 9/2010 | Sowinski et al. |
| 7,806,922 B2 | 10/2010 | Henderson et al. |
| 7,815,628 B2 | 10/2010 | Devens, Jr. |
| 7,828,780 B2 | 11/2010 | Chu et al. |
| 7,832,406 B2 | 11/2010 | Ellis et al. |
| 7,909,864 B2 | 3/2011 | Sheu et al. |
| 7,918,860 B2 | 4/2011 | Leslie et al. |
| 7,947,059 B2 | 5/2011 | Chin et al. |
| 7,947,073 B2 | 5/2011 | Gellman et al. |
| 8,043,673 B2 * | 10/2011 | Lee ......................... A61L 29/04 428/35.7 |
| 8,048,352 B2 | 11/2011 | Devens, Jr. |
| 8,057,534 B2 | 11/2011 | Boismier et al. |
| 8,080,055 B2 | 12/2011 | Atanasoska et al. |
| 8,105,373 B2 | 1/2012 | Girton et al. |
| 8,168,275 B2 | 5/2012 | Lee et al. |
| 8,221,389 B2 | 7/2012 | Brenner et al. |
| 8,235,209 B2 | 8/2012 | Peck et al. |
| 8,293,349 B1 | 10/2012 | Chen et al. |
| 8,353,867 B2 | 1/2013 | Olson |
| 8,357,177 B2 | 1/2013 | Tomaschko et al. |
| 8,409,240 B2 | 4/2013 | Tripp et al. |
| 8,551,021 B2 | 10/2013 | Voeller et al. |
| 8,608,794 B2 | 12/2013 | Girton et al. |
| 8,617,178 B2 | 12/2013 | Leslie et al. |
| 8,715,339 B2 | 5/2014 | Atanasoska et al. |
| 8,731,351 B2 | 5/2014 | Fairneny et al. |
| 8,784,337 B2 | 7/2014 | Voeller et al. |
| 8,808,726 B2 | 8/2014 | Atanasoska et al. |
| 8,828,022 B2 | 9/2014 | White et al. |
| 8,849,081 B2 | 9/2014 | Fairneny et al. |
| 8,862,242 B2 | 10/2014 | Pianca |
| 8,986,366 B2 | 3/2015 | Girton et al. |
| 9,173,656 B2 | 11/2015 | Shurr et al. |
| 9,180,032 B2 | 11/2015 | Merdan et al. |
| 9,295,830 B2 | 3/2016 | Pianca |
| 9,370,638 B2 | 6/2016 | Lee et al. |

\* cited by examiner

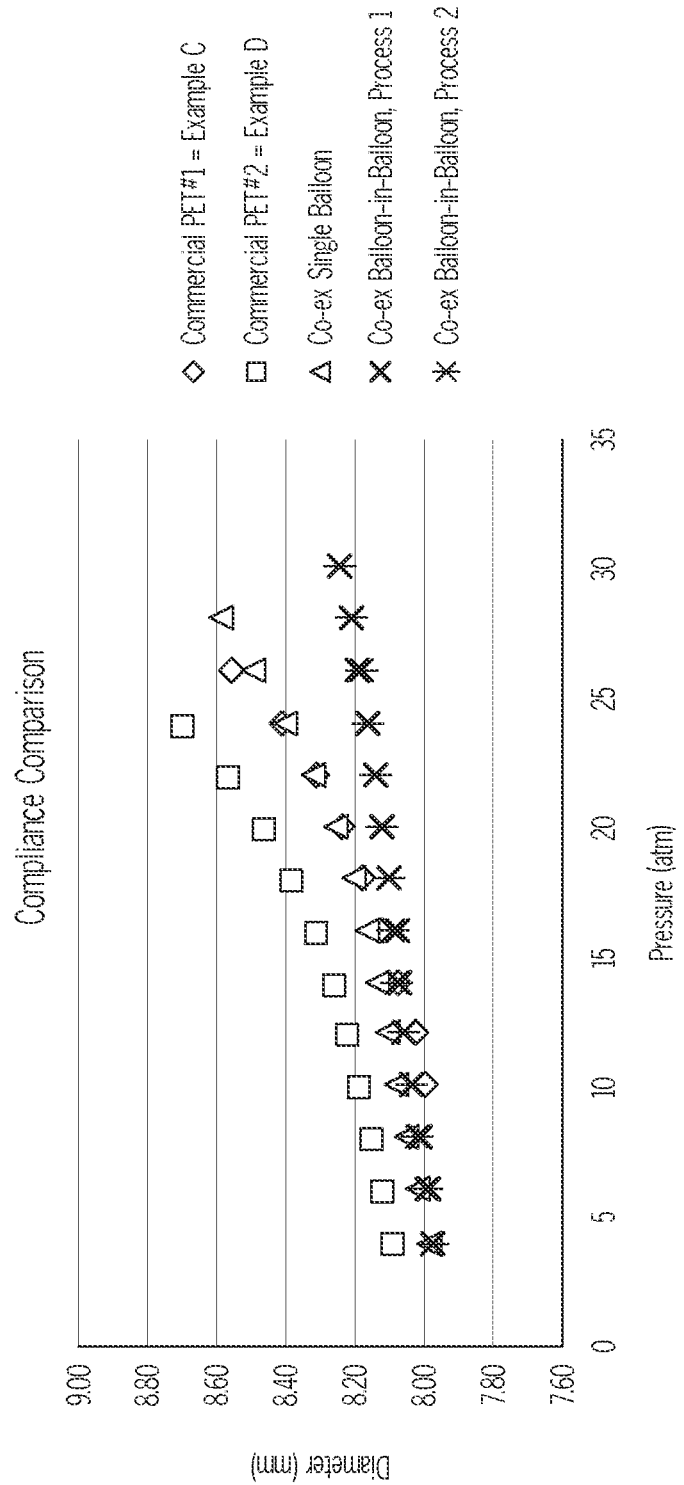

DUAL-LAYER BALLOON DESIGN AND METHOD OF MAKING THE SAME

CROSS REFERENCE TO RELATED APPLICATIONS

This application claims the benefit of U.S. Provisional Patent Application Ser. No. 62/057,666 filed Sep. 30, 2014, the disclosures of each incorporated herein by reference.

BACKGROUND OF THE INVENTION

The present invention relates to expandable medical balloons and methods of making the same.

Expandable medical balloons are employed in a variety of medical procedures including plain old balloon angioplasty (FOB A) as well as for delivery of medical devices to the treatment site such as stent delivery.

Medical applications wherein a balloon is employed intraluminally such as for POBA and stent delivery can be demanding applications due to the extremely small vessels, and the tortuous and long distances the catheter may travel to the treatment site.

For applications where the lesion in the vessel is highly resistant and focalized, such as at the center of a bend in the body vessel, a reduction in burst pressure can be seen with single layer and with dual layer balloons, as well as micro tearing on the exterior of the balloon as a result of localized stress.

Such issues can be even more pronounced when dilatation and/or stenting is being done in the peripheral vasculature.

Compounding the issue even more is that it is typically desirable that the balloon be thin wailed, while still maintaining high strength as most commonly measured by hoop strength or pressure at burst, be relatively inelastic, and have predictable inflation properties.

Inelasticity is desirable to allow for easy control of the diameter, but some elasticity is desirable to enable the surgeon to vary the balloon's diameter as required to treat individual lesions. Suitably, small variations in pressure should not cause wide variation in balloon diameter.

It can be difficult to achieve an excellent balance of properties with a single polymer material. Therefore, a variety of polymer blends and multiple layer polymer balloons have been developed over the years.

There remains a need in the art, however, for an expandable medical balloon having an excellent balance of physical properties.

Without limiting the scope of the invention a brief summary of some of the claimed embodiments of the invention is set forth below. Additional details of the summarized embodiments of the invention and/or additional embodiments of the invention may be found in the Detailed Description of the Invention below.

SUMMARY OF THE INVENTION

In one aspect, the present invention relates to an expandable medical balloon comprising a first balloon wall, the first balloon wall comprising a first balloon layer of polyethylene terephthalate having a first intrinsic viscosity, the first balloon layer is outer to a second balloon layer, the second balloon layer of polyethylene terephthalate having a second intrinsic viscosity, the intrinsic viscosity of the first balloon layer is higher than the intrinsic viscosity of the second balloon layer by about 0.05 dl/g or more.

As defined herein, the term "intrinsic viscosity" shall refer to the capability of a polymer in solution to enhance the viscosity of the solution. The intrinsic viscosity increases with increasing polymer molecular weight.

The intrinsic viscosity number is defined as the limiting value of the specific viscosity/concentration ratio at zero concentration. The viscosity is measured at different concentrations and then extrapolated to zero concentration. Intrinsic viscosity is calculated by determining $\eta_{sp}/C$ and extrapolating to infinite dilution, where C=the concentration of polymer in grams per 100 milliliters of solution.

In some embodiments, the expandable medical balloon may comprise a balloon-in-balloon construction wherein the balloon comprises a second balloon wall that is the inner balloon wall, the first balloon wall is an outer balloon wall, the second balloon wall comprising a first balloon layer of polyethylene terephthalate having a first, intrinsic viscosity, the first layer is an outer layer; and a second balloon layer of polyethylene terephthalate having a second intrinsic viscosity, the second layer is an inner layer, wherein the intrinsic viscosity of the first balloon layer is higher than the intrinsic viscosity of the second balloon layer by about 0.05 dl/g or more The first balloon layer may have an inner diameter hoop ratio of about 6.0 or less as determined by the following formula:

$$\frac{\text{Mold } ID}{\text{Tube } ID}$$

wherein the Tube ID is the inner diameter of the first balloon layer, and the Mold ID is the inner diameter of the balloon mold in which the balloon is formed (inches or mm).

The expandable medical balloon may have an inner diameter hoop ratio of the first balloon outer layer that is 5.5 or less.

The expandable medical balloon may have an overall tubing hoop ratio of the first balloon wall that is equal to or higher than that of the second balloon wall.

The expandable medical balloon may have an intrinsic viscosity of the first balloon layer that is higher than the intrinsic viscosity of the second balloon layer by about 0.10 dl/g or more.

The expandable medical balloon may have a calculated burst strength of about 50,000 psi (344,737,865 Pa) or greater as calculated by the following formula:

$$\text{Strength} = (P \times D/2t)$$

where P=internal pressure when the balloon bursts (psi); D is the exterior diameter (inches) of the balloon when an inflation pressure of 118 psi (813,581 Pa) is applied; and t is the wall thickness (inches) (mm) of the portion of the balloon with the larger exterior diameter (inches or mm).

The expandable medical balloon may have a burst strength of about 50,000 psi (344,737,865 Pa) to about 70,000 psi (482,633,011 Pa).

The expandable medical may have a burst strength of about 55,000 psi (379,211,651Pa) or more.

The expandable medical balloon may have a double wall thickness of about 0.001" (0.0254 mm) to about 0.006" (0.1524 mm).

The expandable medical balloon may have a lower compliance than that of a single layer polyethylene terephthalate balloon of a comparable wall thickness.

The expandable medical balloon may have a volume ratio of the first outer balloon layer to the second balloon inner layer that is about 1:1 to 1:3.

In another aspect, the present invention relates to a method of making an expandable medical balloon including providing a first balloon parison, the first balloon parison is formed from a coextruded tube comprising a first outer layer of polyethylene terephthalate having a first intrinsic viscosity and a second inner layer of polyethylene terephthalate having a second intrinsic viscosity that is less than that of the first intrinsic viscosity of the first outer layer by about 0.05 dl/g or more, inserting the first balloon parison into a balloon mold and radially expanding the first balloon parison in the balloon mold to form a first balloon wall.

The method may further include providing a second balloon parison, the second balloon parison is formed from a coextruded tube comprising a first outer layer of polyethylene terephthalate having a first intrinsic viscosity and a second inner layer of polyethylene terephthalate having a second intrinsic viscosity that is less than that of the first intrinsic viscosity of the first outer layer by about 0.05 dl/g or more and radially expanding the second balloon parison into the first balloon wall in the balloon mold to form a second balloon wall, the second balloon wall is an inner balloon wall and the first balloon wall is an outer balloon wall.

The method may include stretching each of the first balloon parison and second balloon parison prior to inserting each into the balloon mold.

The method may include heat setting the balloon.

The method may have a first balloon layer of each of the first and second coextruded tubes having an intrinsic viscosity that is higher than that of the second balloon layer of each of the first and second coextruded tubes by about 0.10 dl/g or more.

The expandable medical balloon may have a calculated burst strength of about 50,000 psi (344,737,865 Pa) or greater as calculated by the following formula:

Strength=(P×D/2t)

where P=internal pressure when the balloon bursts (psi); D is the exterior diameter (inches) of the balloon when an inflation pressure of 118 psi (813,581 Pa) is applied; and t is the wall thickness (inches) (mm) of the portion of the balloon with the larger exterior diameter.

The expandable medical balloon may have a burst strength of about 50,000 psi (344,737,865 Pa) to about 70,000 psi (482,633,011 Pa).

The expandable medical may have a burst strength of about 55,000 psi (379,211,651Pa) or more.

The expandable medical balloon may have a double wail thickness of about 0.001" (0.0254 mm) to about 0.006" (0.1524 mm).

The method may have a first balloon layer having an inner diameter hoop ratio of about 6.0 or less as determined by the following formula:

$$\frac{Mold\ ID}{Tube\ ID}$$

wherein the Tube ID is the inner diameter of an extruded balloon parison from which the first balloon layer is formed and the Mold ID is determined from the mold in which the first balloon layer is formed.

The method may have a first balloon layer having an inner diameter hoop ratio that is about 5.5 or less.

The method may have an overall tubing hoop ratio of the first balloon wall that is equal to or higher than that of the second balloon wall.

The method may have a volume ratio of the first balloon parison to the second balloon parison of between about 1:1 and about 1:3.

These and other aspects, embodiments and advantages of the present disclosure will become immediately apparent to those of ordinary skill in the art upon review of the Detailed Description and Claims to follow.

BRIEF DESCRIPTION OF THE DRAWINGS

FIG. 1 is a compliance curve illustrating the differences in compliance between single layer balloons, coextruded balloons having one balloon wall and coextruded balloon-in-balloon construction having first and second balloon wails.

DETAILED DESCRIPTION

While embodiments of the present disclosure may take many forms, there are described in detail herein specific embodiments of the present disclosure. This description is an exemplification of the principles of the present disclosure and is not intended to limit the disclosure to the particular embodiments illustrated.

The present invention relates to an expandable medical balloon having at least one first balloon wall including a first balloon layer of polyethylene terephthalate having a first intrinsic viscosity, the first layer is an outer layer; and a second balloon layer of polyethylene terephthalate having a second intrinsic viscosity, the second layer is an inner layer, wherein the intrinsic viscosity of the first balloon layer is higher than the intrinsic viscosity of the second balloon layer by about 0.05 dl/g or more.

In some embodiments, the expandable medical has a balloon-in-balloon construction and further includes a second balloon wall including inner balloon wall and the first balloon wall is an outer balloon wall, the second balloon wall comprising a first balloon layer of polyethylene terephthalate having a first intrinsic viscosity, the first layer is an outer layer and a second balloon layer of polyethylene terephthalate having a second intrinsic viscosity, the second layer is an inner layer, wherein the intrinsic viscosity of the first balloon layer is higher than the intrinsic viscosity of the second balloon layer by about 0.05 dl/g or more.

The layers of the balloon wall have different intrinsic viscosities, i.e. different molecular weights wherein the higher intrinsic viscosity material is the first balloon outer layer.

The method and balloon construction herein does not preclude the use of more than two layers providing that the first layer of the balloon as disclosed herein is outer to the second layer of the balloon as disclosed herein.

The intrinsic viscosity of the first balloon layer which is outer to a second balloon layer is about 0.05 dl/g higher or more than the intrinsic viscosity of the second balloon layer, suitably about 0.75 dl/g higher or more than that of the second balloon layer and most suitably about 0.10 dl/g higher or more than that of the second balloon layer.

The intrinsic viscosity of the first balloon outer layer is suitably about 0.80 dl/g to about 1.20 dl/g and more suitably about 0.90 dl/g to about 1.1 dl/g and the intrinsic viscosity of the inner layer is suitably about 0.75 dl/g to about 0.90 dl/g, and suitably about 0.75 dl/g to about 0.85 dl/g.

The first balloon outer layer has an inner diameter hoop ratio of about 6.0 or less as determined by the following formula:

$$\frac{\text{Mold ID}}{\text{Tube ID}}$$

wherein the Tube ID is the inner diameter of an extruded balloon parison from which the first balloon layer is formed and the Mold ID is determined from the mold in which the first balloon layer is formed. More suitably, the inner diameter hoop ratio of the outer balloon layer is about 5.5 or less, and more suitably less than 5.5 and most suitably about 5.0 or less.

The calculated burst strength of the expandable medical balloon formed herein is about 50,000 psi (344,737,865 Pa) or more, suitably about 50,000 psi (344,737,865 Pa) to about 70,000 psi (482,633,011 Pa), more suitably greater than 50,000 psi (344,737,865 Pa), even more suitably about 55,000 psi (379,211,651 Pa) or more, and most suitably about 60,000 psi (413,685,438 Pa) or more as calculated by the following formula:

Strength=$(P \times D/2t)$ where P=internal pressure when the balloon bursts (psi); D is the exterior diameter (inches) of the balloon when an inflation pressure of 118 psi (813,581 Pa) is applied; and t is the wall thickness of the portion of the balloon with the larger exterior diameter (inches) (mm).

In some embodiments, the calculated burst strength was greater than 65,000 psi (448,159,224 Pa).

The balloons typically have a double wall thickness of about, 0,0005" (0.0127 mm) to about 0.0060" (0.1524 mm), suitably about 0.0010" (0.0254 mm) to about 0.0040" (0.1016 mm), and more suitably about 0.0025" (0.0635 mm) to about 0.0035" (0.0889 mm).

The balloons may be formed by providing a first balloon parison, the first balloon parison is formed from a first coextruded tube comprising a first outer layer of polyethylene terephthalate having a first intrinsic viscosity and a second inner layer of polyethylene terephthalate having a second intrinsic viscosity that is less than that of the first intrinsic viscosity of the first outer layer by about 0.05 dl/g or more, radially expanding the first balloon parison in a balloon mold to form a first balloon wall.

In some embodiments, the balloons may be formed by further providing a second balloon parison, the second balloon parison is formed from a second coextruded tube comprising a first outer layer of polyethylene terephthalate having a first intrinsic viscosity and a second inner layer of polyethylene terephthalate having a second intrinsic viscosity that is less than that of the first intrinsic viscosity of the first outer layer by about 0.05 dl/g or more, inserting the stretched second balloon parison into the first balloon layer and radially expanding the second balloon parison into the first balloon layer in the balloon mold to form a second balloon wall, the second balloon wall is an inner balloon wall and the first balloon wall is an outer balloon wall.

The first and second balloon walls are movable relative to one another and a space may exist between the first and second balloon walls.

Suitably, the first balloon parison, the second balloon parison or both are stretched prior to insertion into the mold and more suitably both the first balloon parison and the second balloon parison are stretched prior to insertion into the mold.

The stretch ratio may he between about 1.5 to about 5.0 times the original length of the tube and suitably about 2 times to about 4 times the original length of the tube.

Balloons having a diameter of about 3 mm to about 12 mm can be formed according to the method disclosed herein.

The first outer layer to the second inner layer volume ratio is about 50% and about 50% or 1:1, more suitably about 30% and about 70% and most suitably about 33% to about 67%) or about 1:2 to about 2:1.

The balloons disclosed herein may have a lower compliance than that of a single layer polyethylene terephthalate balloon of a comparable wall thickness.

Compliance, as used herein, is the term used to describe the degree to which a high-pressure balloon's diameter changes, in inches or millimeters, as a function of pressure.

Low compliance, high pressure balloons, for example, may expand only about 5-10% or less when inflated to the balloon's rated burst pressure while a high compliance, high pressure balloons might expand about 15-30% or more when inflated to rated burst pressure. This is intended for illustrative purposes only, and not as a limitation on the scope of the present invention.

The benefits of this co-extruded tubing design and its application in dual-layer balloon structure are shown in Examples 1 and 2, and Comparative Examples A and B. Both examples have demonstrated the higher intrinsic viscosity of the first outer tubing layer increases burst strength significantly.

EXAMPLES

Example 1

A coextruded tube having an inner diameter (ID) of 0.0392 inches (0.99568 mm) and an outer diameter (OD) of 0.0733 inches (1.862 mm) from two layers of two different grades of PET was radially expanded to form a balloon. The first outer layer was Auriga 5800 PET resin (Auriga Polymers Inc., Charlotte, N.C.) with an intrinsic viscosity (IV) of 0.92 dl/g. The outer layer ID hoop ratio was 4.92. The inner layer was Auriga 2201 PET resin (Auriga Polymers Inc., Charlotte, N.C.) with an intrinsic viscosity (IV) of 0.82 dl/g. The outer layer to the inner layer volume ratio in the tube was 33% to 67%.

The coextruded tube was stretched to 2× its original length (2.0 stretch ratio) at 85° C and 120 psi (827,371 Pa) pressure. The stretched tube was inserted into an 8 mm balloon mold to form 8×40 mm balloon (diameter×length) at 95° C., The balloon forming pressure was 150 psi (1,034,214 Pa) to 250 psi (1,723,689 Pa) and tension was 500 grams. The measured balloon double wall thickness was 0.00178" (0,45212 mm). The compliance curve showed balloon growth from 8 to 20 atmospheres (arm) of 2.6%. The balloon burst strength calculated from its burst pressure, body wall thickness and diameter was 57,237 psi (394,635,223 Pa) (burst pressure was 320.6 psi/2,210,459 Pa) as calculated by the following formula:

Burst strength=(Burst Pressure×Diameter)/(2×Balloon Wall Thickness)

Comparative Example A

A single layer PET tube was extruded with an ID of 0.0410 inches (1.0414 mm) and an OD of 0.0760 inches (1.9304 mm) from Auriga 2201PET resin. The PET tube was then stretched to 2.5× its original length (2.5 stretch ratio) at 85° C and 90 psi (620,528 Pa) pressure. The stretched tube was inserted into an 8 mm balloon mold to form 8×40 balloon at 95° C. The balloon forming pressure was 175 to 275psi and tension was 300 grams. The measured balloon double wall thickness was 0.00188" (0.47752 mm). The compliance curve showed balloon growth from 8 to 20 atm of 2.3%. The balloon burst strength was 53,055 psi (365,801,348 Pa) (burst pressure was 317.6psi/2,189,775 Pa). Comparing to the coextruded balloon in Example 1, this balloon had about 4000 psi (27,579,029 Pa) lower burst strength than that of the coextruded balloon of comparable wail thickness.

Example 2

The same PET 5800/2201 coextruded tubing structure was used as in Example 1. For example 2, however, a balloon-in-balloon construction having a first outer balloon wall and a second inner balloon wall was formed wherein each balloon wall is formed separately from two coextruded tubular balloon parisons.

Balloon outer wall tubing was PET 5800/PET 2201 having a volume ratio of 33%:67% outer layer to the inner layer volume ratio with ID of 0.0392" (0.99568 mm), OD of 0.0733" (1.86182 mm) and the outer layer ID hoop ratio of 4.92.

The balloon inner wall tubing was PET 5800/PET 2201 having a volume ratio of 25%/75% outer layer to the inner layer volume ratio with an ID of 0.0410" (1.0414 mm), an OD of 0.0686" (1.74244 mm) and an outer layer ID hoop ratio of 5.01.

Both of the outer layer tube and the inner layer tube were stretched at 2.0× stretch ratio at 85° C, first at 90 psi (620,528 Pa) for the balloon outer layer tubing and then at 70psi (482,633 Pa) for the balloon inner layer tubing.

The stretched tube of the balloon outer wall, was inserted into an 8 mm balloon mold to form the first 8×40 balloon wall with 150 psi (1,034,214 Pa) to 250 psi (1,723,689 Pa) to 500 psi (3,447,379 Pa) forming pressure at 95° C.

The stretched tube of balloon inner wall was inserted into the first formed balloon wall and radially expanded in the balloon mold forming second balloon wall at 95° C. and 140 psi (965,266 Pa) to 280 psi (1,930,532 Pa) to 450 psi (3,102,640 Pa). The dual-wall balloon was heat set at 125° C for 60 seconds under the pressure of 350 psi (2,413,165 Pa) and tension of 500 grams wherein the second balloon wall was the inner balloon wall and the first balloon wall is the outer balloon wall.

The finished balloon had double wall thickness of 0.00285" (0.07239 mm). The compliance curve showed balloon growth from 8 to 20 arm of 1.6% and 8 to 30 arm of 3.5%. The balloon burst strength was 65,044 psi (448,462,593 Pa) (with burst pressure of 587.3 psi).

Comparative Example B

Two single layer tubes were used for forming the dual-wall balloon. The balloon outer wall tubing was PET 2201 having an ID of 0.0392" (0.99568 mm) and an OD of 0.0772" (1.96088 mm). The balloon inner wall tubing was PET 2201 having an ID of 0.0410" (1.0414 mm) and an OD of 0.0760" (1.9304 mm). Both tubes were stretched at 2.0× stretch ratio using pressures of 90 psi (620,528 Pa) for the balloon outer wall tubing and at 70 psi (482,633 Pa) for the balloon inner wall tubing. The stretched tube of the balloon outer wall was inserted into an 8 mm balloon mold to form the first 8×40 balloon with 175 psi (1,206,583 Pa) to 275 psi (1,896,058 Pa) forming pressure at 95° C. The stretched tube of the balloon inner wall was then inserted into the first formed balloon and radially expanded forming the second balloon inner wall at 95° C and 200 psi (1,378,941 Pa) to 250 psi (1,723,689 Pa). The resultant dual-wall balloon was heat set at 125° C. for 20 seconds under the pressure of 275 psi (1,896,058 Pa) and tension of 300grams. The finished balloon had double wall thickness of 0.00359". The compliance curve showed balloon growth from 8 to 20 atm of 1.3% and 8 to 30 atm of 2.7%. The balloon burst strength was 56,221 psi (387,630,150 Pa) (with burst pressure of 640.2 psi/4,414,024Pa). This balloon burst strength was 8800 psi (60,673,864 Pa) less than the dual-wall balloon formed in Example 2.

Examples 3-5 and Comparative Examples C and D

Table 1 below summarizes burst pressure and calculated burst strength results from testing single wall 8×40 mm commercially available balloons made in production, and coextruded balloons having single and double wall construction using the balloon-in balloon construction method. All the balloons were 8×40 mm. Comparative C and D are single layer commercially available balloons. Example 3 is a one wall coextruded balloon and Examples 4 and 5 are balloon-in balloon construction.

TABLE 1

| Example | Layer #/ Wall # | Balloon 2x wall thickness | Burst Pressure | Calculated Burst Strength |
|---|---|---|---|---|
| C | 1/1 | 0.00270" (0.06858 mm) | 309 psi ($2.1 \times 10^6$ Pa) | 36,181 psi ($2.5 \times 10^8$ Pa) |
| D | 1/1 | 0.00347" (0.008814 mm) | 393 psi ($2.7 \times 10^6$ Pa) | 36,294 psi ($2.5 \times 10^8$ Pa) |
| 3 | 2/1 | 0.00282" (0.07163 mm) | 427 psi ($2.9 \times 10^6$ Pa) | 48,003 psi ($3.3 \times 10^8$ Pa) |
| 4 | 2/2 | 0.00334" (0.08484 mm) | 631 psi ($4.4 \times 10^6$ Pa) | 59,529 psi ($4.1 \times 10^8$ Pa) |
| 5 | 2/2 | 0.00313" (0.07950 mm) | 659 psi ($4.5 \times 10^6$ Pa) | 66,343 psi ($4.6 \times 10^8$ Pa) |

Example 3, the coextruded two-layer single wall balloon wherein the outer PET layer has a higher intrinsic viscosity than the inner PET layer is 33% stronger than the standard single layer balloons of Comparative Examples C and D having similar balloon wall thicknesses.

Example 4 which is a balloon-in-balloon construction is having 2 balloon walls formed from two tubes of coextruded PET having an outer PET layer with a higher intrinsic viscosity than an inner PET layer is 23% stronger than the coextruded balloon of example 3.

Example 5 is a coextruded dual-layer balloon-in-balloon construction wherein a first coextruded tubular parison having an outer PET layer with a higher intrinsic viscosity than an inner PET layer is radially expanded in a balloon to form a first balloon wall and a second coextruded tubular parison having an outer PET layer with a higher intrinsic viscosity than an inner PET layer is radially expanded in the balloon mold into the first balloon wall to form a second inner balloon wall. This balloon was 38% stronger than the balloon-in-balloon of example 3.

Overall, the balloon of example 5 was 83% stronger than a conventional balloon as in comparative examples C and D.

FIG. 1 is a compliance curve illustrating the differences between single layer balloons, coextruded balloons and dual-layer balloon-in-balloon formed balloons.

The coextruded single wall balloon has a similar compliance to the standard single wall balloons, the coextruded balloon-in-balloon had a much lower compliance and the processing method employed showed little impact on balloon compliance as long as they are balloon-in-balloon.

All published documents, including all US patent documents and US patent publications, mentioned anywhere in this application are hereby expressly incorporated herein by reference in their entirety. Any copending patent applications, mentioned anywhere in this application are also hereby expressly incorporated herein by reference in their entirety. Citation or discussion of a reference herein shall not be construed as an admission that such is prior art.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

The invention claimed is:

1. An expandable medical balloon, the expandable medical balloon comprising:
   a first balloon wall, the first balloon wall comprising a first balloon layer of polyethylene terephthalate having a first intrinsic viscosity, the first layer is outer to a second balloon wall, the second balloon wall comprising a second balloon layer of polyethylene terephthalate, the second balloon layer of polyethylene terephthalate having a second intrinsic viscosity, the second layer is an inner layer, wherein the intrinsic viscosity of the first balloon layer is higher than the intrinsic viscosity of the second balloon layer by about 0.05 dl/g or more;
   wherein a volume ratio of the first balloon wall outer layer to the second balloon wall inner layer is about 1:1 to about 1:3.

2. The expandable medical balloon of claim 1 comprising a balloon-in-balloon construction, the expandable medical balloon further comprising a second balloon wall, the second balloon wall is an inner balloon wall and the first balloon wall is an outer balloon wall, the second balloon wall comprising a first balloon layer of polyethylene terephthalate having a first intrinsic viscosity, the first layer is an outer layer; and a second balloon layer of polyethylene terephthalate having a second intrinsic viscosity, the second layer is an inner layer, wherein the intrinsic viscosity of the first balloon layer is higher than the intrinsic viscosity of the second balloon layer by about 0.05 dl/g or more.

3. The expandable medical balloon of claim 1 wherein the first balloon outer layer has an inner diameter hoop ratio of about 6.0 or less as determined by the following formula:

$$\frac{\text{Mold ID}}{\text{Tube ID}}$$

wherein the Tube ID is the inner diameter of an extruded balloon parison from which the first balloon layer is formed and the Mold ID is determined from the mold inner diameter in which the first balloon layer is formed.

4. The expandable medical balloon of claim 3 wherein the inner diameter hoop ratio of the outer balloon layer about 5.5 or less.

5. The expandable medical balloon of claim 2 wherein an overall tubing hoop ratio of the first balloon wall is equal to or higher than that of the second balloon wall as determined by the following formula:

$$\frac{\text{Mold ID}}{\text{Tube ID}}$$

wherein the Tube ID is the inner diameter of an extruded balloon parison from which the first balloon layer is formed and the Mold ID is determined from the mold inner diameter in which the first balloon layer is formed.

6. The expandable medical balloon of claim 5 wherein the overall tubing hoop ratio of the first balloon wall is higher than that of the overall tubing hoop ratio of the second balloon wall.

7. The expandable medical balloon of claim 1 wherein the intrinsic viscosity of the first balloon layer is about 0.10 dl/g higher or more than the intrinsic viscosity of the second balloon layer.

8. The expandable medical balloon of claim 1 wherein a calculated burst strength is about 50,000 psi or greater as calculated by the following formula:

$$\text{Strength} = (P \times D/2t)$$

where P = internal pressure when the balloon bursts (psi); D is the exterior diameter (inches) of the balloon when an inflation pressure of 118 psi is applied; and t is the wall thickness of the portion of the balloon with the larger exterior diameter.

9. The expandable medical balloon of claim 8 wherein the calculated burst strength is about 50,000 psi to about 70,000 psi.

10. The expandable medical balloon of claim 8 wherein the calculated burst strength is about 55,000 psi or more.

11. The expandable medical balloon of claim 1 wherein the balloon has a double wall thickness of about 0.001" to about 0.006".

12. The expandable medical balloon of claim 1 wherein the expandable medical balloon has a lower compliance than that of a single layer polyethylene terephthalate balloon of a comparable wall thickness.

13. An expandable medical balloon, the expandable medical balloon comprising:
   a first balloon wall, the first balloon wall comprising a first balloon layer of polyethylene terephthalate having a first intrinsic viscosity, the first layer is outer to a second layer of polyethylene terephthalate, the second balloon layer of polyethylene terephthalate having a second intrinsic viscosity, the second layer is an inner layer, wherein the intrinsic viscosity of the first balloon layer is higher than the intrinsic viscosity of the second balloon layer by about 0.05 dl/g or more; and
   wherein the expandable medical balloon has a double wall thickness of about 0.001 inches to about 0.006 inches, and has a lower compliance than that of a single layer polyethylene terephthalate balloon of a comparable wall thickness.

14. An expandable medical balloon, the expandable medical balloon comprising:
   a first balloon wall, the first balloon wall comprising a first balloon layer of polyethylene terephthalate having a first intrinsic viscosity, the first layer is outer to a second balloon wall, the second balloon wall comprising a second balloon layer of polyethylene terephthalate, having a second intrinsic viscosity, the second layer is an inner layer, wherein the intrinsic viscosity of the first balloon layer is higher than the intrinsic viscosity of the second balloon layer by about 0.05 dl/g or more; and wherein the intrinsic viscosity of the first balloon wall outer layer is about 0.80 dl/g to about 1.20 dl/g wherein the intrinsic viscosity of the second balloon wall inner layer 0.75 dl/g to about 0.90 dl/g.

15. The expandable medical balloon of claim 14, wherein the intrinsic viscosity of the first balloon wall outer layer is about 0.90 dl/g to about 1.1 dl/g and the intrinsic viscosity of the second balloon wall inner layer is about 0.75 dl/g to about 0.85 dl/g.

* * * * *